United States Patent
Rösmann

(10) Patent No.: US 9,024,588 B2
(45) Date of Patent: May 5, 2015

(54) EMERGENCY POWER SUPPLY MECHANISM AND PROCEDURE FOR THE EMERGENCY POWER SUPPLY

(75) Inventor: Tobias Rösmann, Dortmund (DE)

(73) Assignee: Moog Unna GmbH, Unna (DE)

( * ) Notice: Subject to any disclaimer, the term of this patent is extended or adjusted under 35 U.S.C. 154(b) by 371 days.

(21) Appl. No.: 13/470,208

(22) Filed: May 11, 2012

(65) Prior Publication Data

US 2012/0286738 A1 Nov. 15, 2012

(30) Foreign Application Priority Data

May 12, 2011 (EP) .................................... 11165799

(51) Int. Cl.
*H02J 7/00* (2006.01)
*G08B 21/00* (2006.01)
*G01N 27/02* (2006.01)
*G01N 27/416* (2006.01)
*H02J 9/06* (2006.01)

(52) U.S. Cl.
CPC ................ *H02J 9/061* (2013.01); *G08B 21/00* (2013.01); *G01N 27/02* (2013.01); *H02J 7/00* (2013.01); *G01N 27/416* (2013.01); *Y02B 10/72* (2013.01)

(58) Field of Classification Search
CPC ............ H02J 7/00; H02J 9/061; G08B 21/00; G01N 27/02; G01N 27/416; Y02B 10/72
USPC .................. 320/134, 136, 166; 324/426, 439; 340/636.17
See application file for complete search history.

(56) References Cited

U.S. PATENT DOCUMENTS

| 5,898,234 | A * | 4/1999 | Kitagawa ........................ 307/48 |
| 6,175,511 | B1 | 1/2001 | Ooba |
| 6,707,271 | B2 * | 3/2004 | Kitagawa ...................... 320/134 |
| 7,683,752 | B1 | 3/2010 | Huss |
| 7,750,597 | B2 * | 7/2010 | Takada et al. ................. 320/101 |
| 8,305,045 | B2 * | 11/2012 | Maeagawa .................... 320/162 |
| 8,508,232 | B2 * | 8/2013 | Yugou et al. .................. 324/426 |
| 8,610,405 | B2 * | 12/2013 | Yamazaki et al. ............ 320/134 |

(Continued)

FOREIGN PATENT DOCUMENTS

DE    102009022027 A1 * 11/2010 ................ H02J 7/00

OTHER PUBLICATIONS

Chinese Patent Document No. CN 1819395 A, published Aug. 2006, 3 pages, front page and 1 drawing fig. only.*

(Continued)

*Primary Examiner* — Phallaka Kik
(74) *Attorney, Agent, or Firm* — International IP Law Group, PLLC

(57) ABSTRACT

An emergency power supply device is provided to supply emergency power to a direct voltage circuit. The direct voltage circuit has a first potential tap and a second potential tap, comprising an energy storage unit. The energy storage unit has a plus pole and a minus pole, and one of the poles is connected to the first potential tap via a first connection. The other pole is connected to the second potential tap via a second connection. At least one of the connections has a directional electric current meter and at least one of the connections has an interrupter. The directional electric current meter can measure a flow of charging current. The interrupter can prevent a flow of charging current, and the interrupter can be controlled as a function of the flow of charging current that has been measured.

9 Claims, 3 Drawing Sheets

(56) References Cited

U.S. PATENT DOCUMENTS

| | | | | |
|---|---|---|---|---|
| 8,648,572 | B2* | 2/2014 | Kiyohara et al. | 320/134 |
| 8,806,271 | B2* | 8/2014 | Yong et al. | 714/14 |
| 2002/0070707 | A1* | 6/2002 | Sato | 320/134 |
| 2002/0171399 | A1* | 11/2002 | Kitagawa | 320/134 |
| 2003/0075211 | A1* | 4/2003 | Makita et al. | 136/244 |
| 2003/0169078 | A1* | 9/2003 | Onishi | 327/50 |
| 2004/0155697 | A1* | 8/2004 | Aihara et al. | 327/530 |
| 2005/0135030 | A1* | 6/2005 | Jonas et al. | 361/71 |
| 2005/0242821 | A1* | 11/2005 | Suzuki et al. | 324/430 |
| 2006/0084419 | A1* | 4/2006 | Rocamora et al. | 455/419 |
| 2006/0119368 | A1* | 6/2006 | Sela et al. | 324/522 |
| 2007/0076777 | A1* | 4/2007 | Kao et al. | 372/101 |
| 2007/0276613 | A1* | 11/2007 | Kim | 702/34 |
| 2008/0174926 | A1* | 7/2008 | Evans et al. | 361/90 |
| 2008/0278116 | A1* | 11/2008 | Matsunaga | 320/134 |
| 2010/0204850 | A1* | 8/2010 | Henderieckx | 700/297 |
| 2011/0074356 | A1* | 3/2011 | Yamazaki et al. | 320/134 |
| 2011/0133571 | A1* | 6/2011 | Kiyohara et al. | 307/130 |
| 2011/0166728 | A1* | 7/2011 | Gale et al. | 701/22 |
| 2011/0253402 | A1* | 10/2011 | Aradachi et al. | 173/46 |
| 2012/0169123 | A1* | 7/2012 | Kim | 307/60 |
| 2014/0167529 | A1* | 6/2014 | Teising et al. | 307/134 |

OTHER PUBLICATIONS

US 8,760,121, 06/2014, Utsuno (withdrawn)*

* cited by examiner

EMERGENCY POWER SUPPLY MECHANISM AND PROCEDURE FOR THE EMERGENCY POWER SUPPLY

CROSS-REFERENCE TO RELATED APPLICATION

This application claims priority to European (EP) Patent Application No. 11/165,799, filed on May 12, 2011, the contents of which are incorporated by reference as if set forth in their entirety herein.

BACKGROUND

The terms "first connection" and "second connection" as used here refer to electrically conductive connections. Through these connections, the energy stored in the energy storage unit can be tapped via the poles of the energy storage unit and made available to the direct voltage circuit at the potential taps in the form of a direct voltage.

Emergency power supply devices for supplying emergency power to a direct voltage circuit find widespread use in the state of the art. A frequent application case is the supply of emergency power to the intermediate circuit of a converter. As a rule, such converters are supplied with three-phase alternating current from an external power network and they supply a consumer, for instance, a motor, with alternating current or direct current. When the three-phase alternating current provided by the external power network is converted, first of all, the three-phase alternating current is rectified. The direct current generated by the rectification is applied to an internal direct current circuit in the inverter. This direct current circuit is referred to as an intermediate circuit. The direct voltage present in the direct current circuit can be tapped via a first potential tap and via a second potential tap. An alternating current for supplying a consumer is generated from the direct voltage that is present in the intermediate circuit, for example, by means of inversion. In the case of safety-relevant consumers, the consumer continues to operate, at least for a certain period of time, even if the external power network fails. Examples of safety-relevant consumers include the motors employed in passenger elevators or the motors of the pitch system of wind turbines.

If the external power network fails, which can happen, for example, in case of a fire in a building, the elevators travel to the next floor and open the doors without the power supplied by the external power network, so that the persons in the elevator can be brought to safety. Conventional drive motors for elevators are supplied with power by means of converters. In order for elevators to be able to perform the above-mentioned emergency procedure in case of a power failure, they are normally equipped with an emergency power supply device that can supply the converter with power in case of an emergency.

Modern wind turbines are usually equipped with electric pitch systems that have a motor as well as a converter to supply power to the motor for each rotor blade. As a rotor blade rotates around its longitudinal axis, such pitch systems regulate the position of the rotor blades relative to the wind, and they are often the only safe way to bring the rotor of a wind turbine to a standstill. This is done in that the pitch system turns the rotor blades into a feathering position, bringing the rotor to a standstill because it is no longer driven by the wind. The pitch system is normally supplied with power by the power network into which the wind turbine also feeds the power it generates. If the power network fails, a hazardous situation can arise, for example, if the rotational speed of the rotor of the wind turbine exceeds the permissible maximum value if the wind picks up, so that the wind turbine could sustain damage or persons present in the vicinity could suffer injury as a result.

In order to avert such a hazardous situation, even if the power network fails, the rotor blades may be moved into the feathering position, even when the pitch system is not being supplied with power by the external power network. For this purpose, it is known from the state of the art to equip the pitch system with an emergency power supply device that, in case of a power network failure, ensures the supply of power to the pitch system and thus the functionality of the pitch system, at least until the rotor blades have been moved into the safe feathering position. With a direct-current motor, the emergency power supply device can also be connected directly to the direct-current motor in case of an emergency.

However, a safety problem arises when an emergency power supply device is connected to the intermediate circuit of a converter. Batteries are often employed as the emergency power supply device. Since the intermediate circuit can have a variable voltage that can also be far higher than the voltage provided by the battery, the batteries usually are not connected directly to the intermediate circuit in order to avoid overcharging of the batteries. In order to prevent a flow of charging current from the intermediate circuit into the batteries, one or more decoupling components are installed in the connection lines between the poles of the battery and the potential taps of the intermediate circuit. Therefore, the task of the decoupling components is to prevent a current flow that corresponds to a charging of the batteries, that is to say, a flow of charging current, but at the same time, to allow a flow of current that corresponds to a discharging of the batteries, that is to say, a flow of discharging current. A flow of discharging current corresponds to precisely the proper use of the batteries, namely, the supply of emergency power to the direct current circuit in case of an emergency. As a rule, diodes or diodes connected in series are used for decoupling purposes and, in view of their function as a decoupling component, they are also referred to as decoupling diodes. The diodes employed may be power diodes, which are used for high voltages and currents. An alternative to the utilization of batteries as the emergency power supply device is the use of capacitors. However, like batteries, capacitors can also be damaged by excessively high voltages provided by the intermediate circuit.

Component defects, ageing processes or overloading, for example, can cause the employed decoupling components to fail. Extraordinarily high voltages in the reverse direction of the decoupling components are a major cause of such a possible failure of the decoupling components. A failure can especially consist of a breakdown in an employed decoupling diode. Such a breakdown causes the decoupling diode to become conductive in the reverse direction, so that it is no longer capable of preventing a flow of charging current. If the failure of the decoupling components results in an uncontrolled flow of charging current, the batteries can become overcharged. Outgassing of hydrogen from the batteries can occur if the batteries are overcharged. This constitutes a major safety hazard since the hydrogen gas can form an explosive mixture with the ambient atmosphere, which can easily be ignited by the sources of ignition commonly found in wind turbines. If the batteries are located in a closed container, the pressure build-up inside the container brought about by the outgassing alone can cause the container to rupture, which can lead to considerable damage inside the wind turbine, also due to the subsequent ignition of the hydrogen gas that has escaped from the ruptured container. In the case of very high pressures, even self-ignition can occur.

SUMMARY

The subject innovation relates to an emergency power supply device to supply emergency power to a direct voltage circuit, whereby the direct voltage circuit has a first potential tap and a second potential tap, comprising an energy storage unit, whereby the energy storage unit has a plus pole and a minus pole, and whereby one of the poles is connected to the first potential tap via a first connection, while the other pole is connected to the second potential tap via a second connection.

In this context, a directional electric current meter is a device that is able to measure the absolute current flowing in a defined direction in one of the electrically conductive connections between the energy storage unit and the direct current circuit. As a result, the directional electric current meter can ascertain whether a charging current that might be harmful to the energy storage unit is flowing. Accordingly, the direction in which the directional electric current meter can measure the current flow is determined on the basis of the installation situation of the directional electric current meter and of the energy storage unit, especially the polarity of the energy storage unit.

Further, the directional electric current meter is able to measure the absolute current flow as well as the direction of the current flow. In this case, the directional electric current meter can distinguish between the presence of a flow of charging current that might be harmful to the energy storage unit, a harmless flow of discharging current or no current flow at all. In the case of a flow of charging current, the interrupter can prevent the current flow. For this purpose, it is provided that the information regarding the measured flow of charging current can be relayed by the directional electric current meter directly to the interrupter or to a superordinated control unit, as a result of which the interrupter can be controlled directly or indirectly via the control unit as a function of the measured flow of charging current.

The emergency power supply device according to the subject innovation can also be employed to detect a flow of charging current caused by a short circuit between the ground potential and the connection of the directional electric current meter to one of the poles of the battery. After all, the flow of charging current caused by such a short circuit likewise flows through the directional electric current meter.

The emergency power supply device according to the subject innovation has the advantage that it is possible to dispense with the use of decoupling components of the type commonly found in the state of the art, thus resulting in a considerable cost advantage. Furthermore, safe operation of the emergency power supply device results from the interaction between the directional electric current meter and the interrupter making it possible to prevent a potentially harmful charging current.

The emergency power supply device according to the subject innovation is not limited to energy storage units that could become damaged by a charging current, but it also allows the controlled charging of energy storage units such as, for instance, capacitors. The fact that the interrupter can prevent a flow of charging current can mean that the interrupter can only switch back and forth between two states, namely, conductive and non-conductive. However, the conductivity of the interrupter can be adjusted within a range between these two extremes, so that a flow of charging current can be controlled with precision.

Further, the directional electric current meter may have a decoupling component, a bypass diode and a current-measuring element, whereby the bypass diode and the current-measuring element are connected in series, while the decoupling component is connected in parallel to the series connection consisting of the bypass diode and the current-measuring element.

Here, the bypass diode is connected in such a way that it allows a potentially harmful charging current to pass through while it blocks a discharging current. This ensures that the current-measuring element measures only charging current flows. For this reason, it is sufficient if the current-measuring element is only capable of performing a simple current measurement and, in particular, cannot detect the direction of the current flow. If the current-measuring element detects an impermissible flow of charging current, the flow of charging current can be prevented by the interrupter. According to the subject innovation, a permissible discharging current flows via the decoupling component and is not detected by the current-measuring element.

Advantageously, existing emergency power supply devices known in the art that have at least one decoupling component can be retrofitted to provide the features of the subject innovation. This is done simply in that, in parallel to the decoupling component that is already present, the series connection consisting of the current-measuring element and the bypass diode is installed and an interrupter, if not already present, is installed.

The interrupter is established by the current-measuring element.

This functional integration of the interrupter into the current-measuring element means that a separate component for the interrupter is not used. Advantageously, connection lines between the current-measuring element and the interrupter are not used. Consequently, the emergency power supply device can be produced inexpensively and simply. The retrofitting of existing emergency power supply devices is likewise simplified.

The current-measuring element has a safety fuse. The presence of a safety fuse inside the current-measuring element enables the integration of the interrupter into the current-measuring element. In this context, the safety fuse is designed in such a way that the current is measured by the safety fuse itself. If only a negligible charging current is flowing or none at all, the safety fuse is in the conductive state. If a charging current that is greater than the tripping current for the safety fuse is flowing, the safety fuse switches over into the non-conductive state. This shows that the safety fuse not only performs a measurement of the current, but also concurrently functions as an interrupter in that it interrupts the current flow if the latter is too high, thus preventing a potentially harmful flow of charging current. All familiar types of safety fuses are an option, including fusible cutouts. In this context, fusible cutouts have the disadvantage that, on the one hand, they are destroyed when they are tripped and cannot be reset into the conductive state but, on the other hand, they offer a very high level of reliability and entail low component costs. In contrast to automatic circuit-breakers, fusible cutouts are capable of safely disconnecting high currents at high voltages.

In one embodiment, the current-measuring element has a PTC thermistor. The term PTC thermistor as used herein refers to a component whose resistance increases as the temperature rises. In particular, the PTC thermistor is designed in such a way that, if the charging current is not negligible, it heats up to such an extent that the resistance which increases as the temperature rises prevents the flow of charging current.

In another embodiment, the current-measuring element is connected to a signal element and information about the status of the current-measuring element can be output by the signal element. Further, it is advantageous for at least one of the connections to have at least one switch, whereby the switch can be controlled as a function of the information about the status of the current-measuring element that can be output by the signal element.

Towards this end, a direct or indirect connection can be provided between the signal element and the switch, by means of which the information about the status of the current-measuring element can be transmitted. Information about the status can comprise concrete measured values such as, for example, current intensity or current direction, and can relate to properties of the current-measuring element, for instance, about the state of readiness of the current-measuring element.

In one embodiment, the direct voltage circuit has a control unit, and the signal element for relaying information about the status of the current-measuring element to the control unit is connected to the control unit. In order to do so, a direct or indirect connection can be provided between the signal element and the control unit, by means of which the information about the status of the current-measuring element can be transmitted. On the basis of the transmitted information, the control unit can control the direct voltage circuit and/or additional devices associated with the control unit. In particular, the control unit can be part of a converter to supply power to one or more consumers and can serve to control the converter and/or the consumer.

In one embodiment, at least one of the connections has a decoupling component. As a rule, the provision of several decoupling components in the connections between the energy storage unit and the direct voltage circuit can further improve the safety of the emergency power supply device.

Advantageously, the directional electric current meter has a decoupling component, a bypass diode, and a current-measuring element, whereby the bypass diode and the current-measuring element are connected in series, while the decoupling component is connected in parallel to the series connection consisting of the bypass diode and the current-measuring element, and whereby the connection between the energy storage unit and the direct voltage circuit in which the directional electric current meter is not provided has an additional decoupling component.

Errors in the direct voltage circuit can cause the voltage level in the direct voltage circuit to rise sharply either briefly or permanently. These voltage peaks are present at the potential taps of the direct voltage circuit where the connections between the energy storage unit and the direct voltage circuit are connected.

Due to the fact that the decoupling component contained in the electric current meter is connected in parallel to the series connection consisting of the bypass diode and the current-measuring element, the decoupling component is largely protected against voltage peaks present in the reverse direction of the decoupling component. Only the additional decoupling component is fully exposed to voltage peaks that occur in the reverse direction. Therefore, as a rule, any failure caused by extraordinarily high voltages occurring in the reverse direction first affects the additional decoupling component. If the additional decoupling component fails in such a way that it becomes conductive, then a flow of charging current can occur for a brief time. This flow of charging current, however, is detected by the current-measuring element and subsequently prevented by the interrupter. Consequently, the occurring charging current provides indirect information about the failure of the additional decoupling component. Therefore, the measurement of the briefly occurring flow of charging current by the current-measuring element indirectly yields information about the failure of the additional decoupling component. This information can be output by the signal element.

In another embodiment, at least one of the decoupling components is formed by at least one diode. The use of multiple diodes connected in series as the decoupling component reduces the probability of failure of one decoupling component as opposed to the use of a single diode since a voltage present in the reverse direction distributes its voltage drop over the multiple diodes so that each individual diode is exposed to a smaller load. Here, the distribution of the voltage drop over the multiple diodes does not take place uniformly but rather asymmetrically.

On the basis of the method for supplying emergency power described above, when an undesired flow of charging current is measured, the interrupter is actuated in such a manner that the interrupter prevents the undesired flow of charging current. In this context, the flow of charging current is normally measured by the directional electric current meter. If a flow of charging current is ascertained that exceeds a negligible value and thus could conceivably be harmful to the energy storage unit, the information about the measured flow of charging current is employed directly or indirectly to actuate the interrupter in such a way that it prevents the potentially harmful flow of charging current.

The method for supplying emergency power is not restricted only to energy storage units that can be damaged by a flow of charging current, but rather it also allows a controlled charging of energy storage units such as, for example, capacitors. For this reason, a flow of charging current can be permitted under certain conditions, for example, when it serves to charge the energy storage unit and/or when it remains within limits that are not harmful to the energy storage unit.

Further, the current-measuring element is connected to a signal element and information about the status of the current-measuring element can be output by means of the signal element.

Additionally, at least one of the connections has at least one switch, whereby the switch is controlled as a function of the information about the status of the current-measuring element output by the signal element. By means of such a switch, the energy storage unit can be disconnected from the direct voltage circuit. Therefore, this disconnection constitutes an additional safety measure so that an undesired flow of charging current can be prevented, even if the functionality of the interrupter is impaired. In particular, the disconnection of the energy storage unit from the direct voltage circuit by means of the switch protects any decoupling components that might have been installed in the connections against loads caused by ongoing high voltages from the direct voltage circuit.

Further, the direct voltage circuit has a control unit and the signal element is connected to the control unit, whereby information about the status of the current-measuring element is relayed to the control unit by the signal element. For this purpose, a direct or indirect connection between the signal element and the control unit can be provided by means of which the information about the status of the current-measuring element is transmitted. On the basis of the transmitted information, the control unit controls the direct voltage circuit and/or additional devices associated with the control unit.

Figure 1:
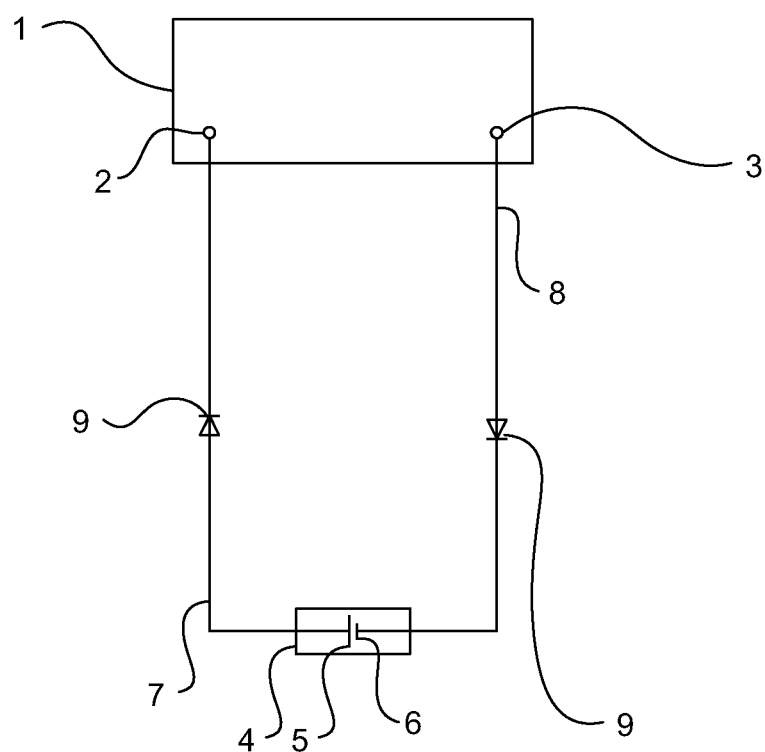
FIG. 1 is a schematic diagram of an emergency power supply device.

The emergency power supply device known from the state of the art depicted in FIG. 1 serves to supply emergency power to a direct voltage circuit (1) with a first potential tap (2) and a second potential tap (3). The energy storage unit (4) of the emergency power supply device has a plus pole (5) and a minus pole (6). Here, the first potential tap (2) of the direct voltage circuit (1) is connected to the plus pole (5) of the energy storage unit (4) via a first connection (7). The second potential tap (3) of the direct voltage circuit (1) is connected to the minus pole (6) of the energy storage unit (4) via a second connection (8). The first connection (7) as well as the second connection (8) each have a decoupling diode (9).

The direct voltage circuit (1) can be supplied with power from the energy storage unit (4) via the first connection (7) and via the second connection (8). The energy storage unit (4) is protected by the decoupling diodes (9) against overcharging. If the decoupling diodes (9) fail, for instance, due to ageing, overload or manufacturing flaws, the energy storage unit (4) is no longer protected against overcharging.

Figure 2:
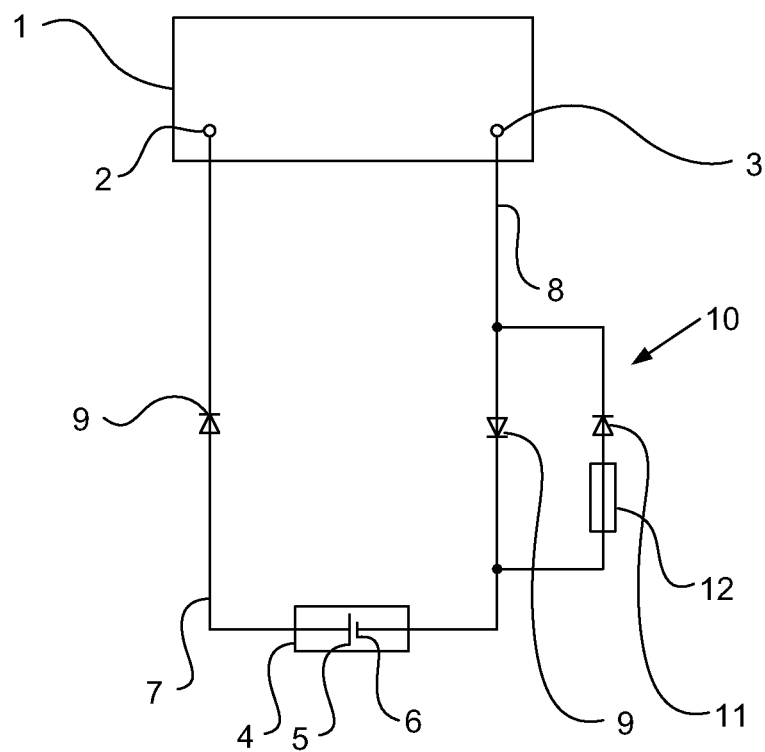
FIG. 2 is a diagram of an emergency power supply device in accordance with an embodiment.

FIG. 2 shows an emergency power supply device with a directional electric current meter (10) and an interrupter. The directional electric current meter (10) is installed in the second connection (8) and it has a decoupling component, a bypass diode (11) and a current-measuring element (12). The decoupling component is formed by a decoupling diode (9). An additional decoupling component (9) is installed in the first connection (7). The current-measuring element (12) is configured as a fusible cutout and consequently also functions as the interrupter. The decoupling component formed by the decoupling diode (9) is connected in parallel to the series connection consisting of the current-measuring element (12) and the bypass diode (11).

The emergency power supply device of FIG. 2 differs from the emergency power supply device of FIG. 1 only by the current-measuring element (12) configured as a fusible cutout and the bypass diode (11). This slight difference from the configuration familiar from the state of the art, which is shown in FIG. 1, makes it easy and inexpensive to retrofit existent emergency power supply devices according to the state of the art. If the additional decoupling diodes (9) arranged in the first connection (7) should fail, a charging current might flow from the minus pole (5) of the energy storage unit (4) via the current-measuring element (12) and the bypass (11) to the second potential tap (3) of the direct voltage circuit (1). If the flow of charging current exceeds a certain value, the fuse that forms the current-measuring element (12) and that functions as an interrupter blows. A further flow of charging current is no longer possible via the decoupling diode (9) in the second connection because this diode is connected for a flow of charging current in the reverse direction.

In the case of a short circuit between the minus pole (6) of the energy storage unit (4) and a ground potential (not shown here), depending on the potential of the second potential tap (3) of the direct voltage circuit (1), a charging current could flow from the ground potential to the second potential tap (3) of the direct voltage circuit (1) via the current-measuring element (12) and the bypass diode (11). Therefore, a flow of charging current caused by such a short circuit can be measured by the current-measuring element (12). If the flow of charging current exceeds a certain value, the fuse that forms the current-measuring element (12) blows, thus interrupting the flow of charging current caused by the short circuit.

By the same token, a short circuit can occur between the plus pole (5) of the energy storage unit (4) and the ground potential (not shown here). If, in this case, the first potential tap (2) of the direct voltage circuit (1) is at a higher potential than the ground potential, a current flow from the first potential tap (2) of the direct voltage circuit (1) to the ground potential is prevented by the decoupling diode (9). If, however, the second potential tap (3) of the direct voltage circuit (1) is at a lower potential than the differential potential between the plus pole (5) and the minus pole (6) of the energy storage unit (4), a charging current can flow via the current-measuring element (12) and the bypass (11). A flow of charging current generated in this manner can also be measured by the current-measuring element (12). If the flow of charging current exceeds a certain value, the fuse that forms the current-measuring element (12) blows, thus interrupting the flow of charging current caused by the short circuit.

Figure 3:
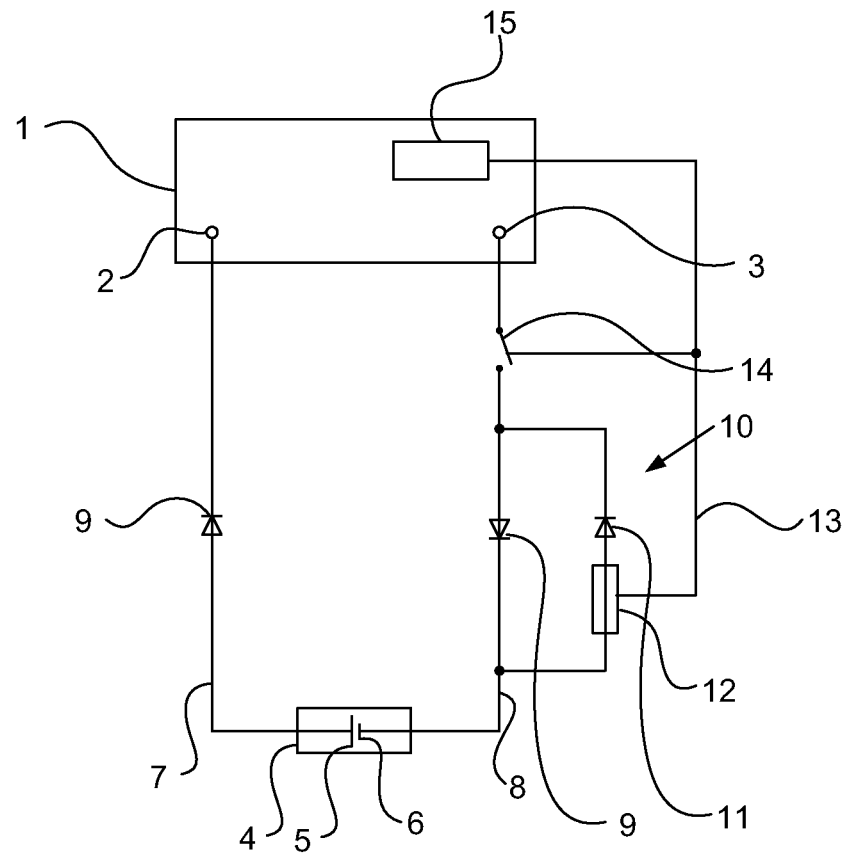
FIG. 3 is a diagram of the emergency power supply device in accordance with an embodiment.

The emergency power supply device shown in FIG. 3 works according to the same principle as the emergency power supply device of FIG. 2. In addition, the emergency power supply device according to FIG. 3 has a signal element (13) by means of which the information about the status of the current-measuring element (12) can be output. The information about the status of the current-measuring element (12) output by the signal element (13) can be made available to a switch (14) arranged in the second connection (8). In this context, the switch (14) can be controlled in such a way that, in the case of a potentially harmful flow of charging current, the switch (14) is opened so that the second connection (8) is safely interrupted, thus reliably protecting the energy storage unit (4) against overcharging.

By the same token, the information about the status of the current-measuring element (12) that has been output by the signal element (13) can be made available to a control unit (15). This control unit (15) is shown in FIG. 3 as part of the direct voltage circuit (1), although it can also be arranged outside of the direct voltage circuit (1).

What is claimed is:

1. An emergency power supply device, comprising:
an energy storage unit, wherein the emergency power supply device supplies emergency power to a direct voltage circuit, and wherein the direct voltage circuit comprises a first potential tap and a second potential tap, and wherein the energy storage unit comprises a plus pole and a minus pole, and wherein one of the plus pole and the minus pole is connected to a first potential tap via a first connection, and wherein an other of the plus pole and the minus pole is connected to the second potential tap via a second connection, and wherein at least one of the connections comprises a directional electric current meter, and wherein at least one of the connections comprises an interrupter, and wherein the directional electric current meter is configured to measure a flow of charging current, and wherein the interrupter is configured to prevent a flow of charging current, and wherein the interrupter is configured to be controlled as a function of flow of the charging current that has been measured and whereby a connection between the energy storage unit and the direct voltage circuit in which a directional electric current meter is not provided has an additional decoupling component that prevents a flow of charging current of the energy storage unit.

2. The emergency power supply device of claim 1 wherein the directional electric current meter comprises:
   a decoupling component;
   a bypass diode; and
   a current-measuring element, wherein the bypass diode and the current-measuring element are connected in a series connection, and wherein the decoupling component is connected in parallel to the series connection.

3. The emergency power supply device of claim 2, wherein the interrupter is established by the current-measuring element.

4. The emergency power supply device of claim 3, wherein the current-measuring element comprises a safety fuse.

5. The emergency power supply device of claim 4, wherein the current-measuring element has a PTC thermistor.

6. The emergency power supply device of claim 2, wherein the current-measuring element is connected to a signal element, and wherein the signal element outputs information about a status of the current-measuring element.

7. The emergency power supply device of claim 6, wherein at least one of the connections comprises at least one switch, wherein the switch is configured to be controlled as a function of the information about the status of the current-measuring element.

8. The emergency power supply device of claim 6, wherein the direct voltage circuit comprises a control unit, and wherein the signal element for relaying information about the status of the current-measuring element to the control unit is connected to the control unit.

9. The emergency power supply device according of claim 2, wherein at least one of the connections comprises a decoupling component and at least one decoupling component is formed by at least one diode.

* * * * *